United States Patent

McCorquodale et al.

Patent Number: 5,610,129
Date of Patent: Mar. 11, 1997

[54] DYE TRANSFER INHIBITING COMPOSITIONS

[75] Inventors: Finlay McCorquodale, Woluwe-St.-Lambert; Alfred Busch, Londerzeel, both of Belgium

[73] Assignee: The Proctor & Gamble Company, Cincinnati, Ohio

[21] Appl. No.: 232,249

[22] PCT Filed: Oct. 28, 1992

[86] PCT No.: PCT/US92/09204

§ 371 Date: May 5, 1994

§ 102(e) Date: May 5, 1994

[87] PCT Pub. No.: WO89/09813

PCT Pub. Date: Oct. 19, 1989

[30] Foreign Application Priority Data

Nov. 6, 1991 [EP] European Pat. Off. .............. 91202882

[51] Int. Cl.$^6$ .............................. C11D 3/386; C11D 7/42
[52] U.S. Cl. .................. 510/320; 510/321; 510/392; 510/530
[58] Field of Search ................. 252/95, 174.12, 252/174.18, DIG. 12; 435/209; 510/320, 321, 392, 530

[56] References Cited

U.S. PATENT DOCUMENTS 4,077,768  3/1978  Johnston et al. ............... 8/107

FOREIGN PATENT DOCUMENTS 9117243  5/1990  WIPO ................. C12N 9/42
9105839  5/1991  WIPO ................. C11D 3/386

*Primary Examiner*—Glenn A. Caldarola
*Assistant Examiner*—Alexander G. Ghyka
*Attorney, Agent, or Firm*—George W. Allen; Robert B. Aylor

[57] ABSTRACT

Dye transfer inhibiting compositions are disclosed, comprising an enzyme exhibiting peroxidase activity, a hydrogen peroxide or a hydrogen peroxide precursor or an enzymatic system capable of generating hydrogen peroxide, an additional oxidizable substrate, and a cellulase, characterized in that the cellulase provides at least 10% removal of immobilized radioactive labelled carboxymethyl cellulose according to C14CMC method at $25 \times 10^{-6}\%$ by weight of the laundry test solution.

According to the present invention, a preferred cellulase consists essentially of a homogeneous endoglucanase component which is immunoreactive with a monoclonal antibody raised against a partially purified=43 kD cellulase derived from *Humicola insolens* DM1800.

14 Claims, No Drawings

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1060 base pairs
        ( B ) TYPE: nucleic acid
        ( C ) STRANDEDNESS: unknown
        ( D ) TOPOLOGY: unknown ( i x ) FEATURE:
        ( A ) NAME/KEY: CDS
        ( B ) LOCATION: 10..924

( x i ) SEQUENCE DESCRIPTION: SEQ ID NO:1:

```
GGATCCAAG ATG CGT TCC TCC CCC CTC CTC CCG TCC GCC GTT GTG GCC                48
          Met Arg Ser Ser Pro Leu Leu Pro Ser Ala Val Val Ala
          1               5                   10

GCC CTG CCG GTG TTG GCC CTT GCC GCT GAT GGC AGG TCC ACC CGC TAC              96
Ala Leu Pro Val Leu Ala Leu Ala Ala Asp Gly Arg Ser Thr Arg Tyr
    15              20                  25

TGG GAC TGC TGC AAG CCT TCG TGC GGC TGG GCC AAG AAG GCT CCC GTG            144
Trp Asp Cys Cys Lys Pro Ser Cys Gly Trp Ala Lys Lys Ala Pro Val
30                  35                  40                      45

AAC CAG CCT GTC TTT TCC TGC AAC GCC AAC TTC CAG CGT ATC ACG GAC            192
Asn Gln Pro Val Phe Ser Cys Asn Ala Asn Phe Gln Arg Ile Thr Asp
                50                  55                  60

TTC GAC GCC AAG TCC GGC TGC GAG CCG GGC GGT GTC GCC TAC TCG TGC            240
Phe Asp Ala Lys Ser Gly Cys Glu Pro Gly Gly Val Ala Tyr Ser Cys
                65                  70                  75

GCC GAC CAG ACC CCA TGG GCT GTG AAC GAC GAC TTC GCG CTC GGT TTT            288
Ala Asp Gln Thr Pro Trp Ala Val Asn Asp Asp Phe Ala Leu Gly Phe
            80                  85                  90

GCT GCC ACC TCT ATT GCC GGC AGC AAT GAG GCG GGC TGG TGC TGC GCC            336
Ala Ala Thr Ser Ile Ala Gly Ser Asn Glu Ala Gly Trp Cys Cys Ala
        95                  100                 105

TGC TAC GAG CTC ACC TTC ACA TCC GGT CCT GTT GCT GGC AAG AAG ATG            384
Cys Tyr Glu Leu Thr Phe Thr Ser Gly Pro Val Ala Gly Lys Lys Met
110                 115                 120                     125

GTC GTC CAG TCC ACC AGC ACT GGC GGT GAT CTT GGC AGC AAC CAC TTC            432
Val Val Gln Ser Thr Ser Thr Gly Gly Asp Leu Gly Ser Asn His Phe
                130                 135                 140

GAT CTC AAC ATC CCC GGC GGC GGC GTC GGC ATC TTC GAC GGA TGC ACT            480
Asp Leu Asn Ile Pro Gly Gly Gly Val Gly Ile Phe Asp Gly Cys Thr
                145                 150                 155

CCC CAG TTC GGC GGT CTG CCC GGC CAG CGC TAC GGC GGC ATC TCG TCC            528
Pro Gln Phe Gly Gly Leu Pro Gly Gln Arg Tyr Gly Gly Ile Ser Ser
            160                 165                 170

CGC AAC GAG TGC GAT CGG TTC CCC GAC GCC CTC AAG CCC GGC TGC TAC            576
Arg Asn Glu Cys Asp Arg Phe Pro Asp Ala Leu Lys Pro Gly Cys Tyr
    175                 180                 185

TGG CGC TTC GAC TGG TTC AAG AAC GCC GAC AAT CCG AGC TTC AGC TTC            624
Trp Arg Phe Asp Trp Phe Lys Asn Ala Asp Asn Pro Ser Phe Ser Phe
190                 195                 200                     205

CGT CAG GTC CAG TGC CCA GCC GAG CTC GTC GCT CGC ACC GGA TGC CGC            672
Arg Gln Val Gln Cys Pro Ala Glu Leu Val Ala Arg Thr Gly Cys Arg
                210                 215                 220

CGC AAC GAC GAC GGC AAC TTC CCT GCC GTC CAG ATC CCC TCC AGC AGC            720
Arg Asn Asp Asp Gly Asn Phe Pro Ala Val Gln Ile Pro Ser Ser Ser
                225                 230                 235

ACC AGC TCT CCG GTC AAC CAG CCT ACC AGC ACC AGC ACG TCC ACC                768
Thr Ser Ser Pro Val Asn Gln Pro Thr Ser Thr Ser Thr Ser Thr
            240                 245                 250

TCC ACC ACC TCG AGC CCG CCA GTC CAG CCT ACG ACT CCC AGC GGC TGC            816
Ser Thr Thr Ser Ser Pro Pro Val Gln Pro Thr Thr Pro Ser Gly Cys
```

```
              255                      260                      265
ACT GCT GAG AGG TGG GCT CAG TGC GGC GGC AAT GGC TGG AGC GGC TGC       864
Thr Ala Glu Arg Trp Ala Gln Cys Gly Gly Asn Gly Trp Ser Gly Cys
270                 275                 280                 285

ACC ACC TGC GTC GCT GGC AGC ACT TGC ACG AAG ATT AAT GAC TGG TAC       912
Thr Thr Cys Val Ala Gly Ser Thr Cys Thr Lys Ile Asn Asp Trp Tyr
            290                 295                 300

CAT CAG TGC CTG TAGACGCAGG GCAGCTTGAG GGCCTTACTG GTGGCCGCAA           964
His Gln Cys Leu
        305

CGAAATGACA CTCCCAATCA CTGTATTAGT TCTTGTACAT AATTTCGTCA TCCCTCCAGG    1024

GATTGTCACA TAAATGCAAT GAGGAACAAT GAGTAC                              1060
```

( 2 ) INFORMATION FOR SEQ ID NO:2:

( i ) SEQUENCE CHARACTERISTICS:
        ( A ) LENGTH: 305 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Arg Ser Ser Pro Leu Leu Pro Ser Ala Val Ala Ala Leu Pro
 1               5                  10                  15

Val Leu Ala Leu Ala Ala Asp Gly Arg Ser Thr Arg Tyr Trp Asp Cys
            20                  25                  30

Cys Lys Pro Ser Cys Gly Trp Ala Lys Lys Ala Pro Val Asn Gln Pro
        35                  40                  45

Val Phe Ser Cys Asn Ala Asn Phe Gln Arg Ile Thr Asp Phe Asp Ala
    50                  55                  60

Lys Ser Gly Cys Glu Pro Gly Gly Val Ala Tyr Ser Cys Ala Asp Gln
65                  70                  75                  80

Thr Pro Trp Ala Val Asn Asp Asp Phe Ala Leu Gly Phe Ala Ala Thr
                85                  90                  95

Ser Ile Ala Gly Ser Asn Glu Ala Gly Trp Cys Cys Ala Cys Tyr Glu
            100                 105                 110

Leu Thr Phe Thr Ser Gly Pro Val Ala Gly Lys Lys Met Val Val Gln
        115                 120                 125

Ser Thr Ser Thr Gly Gly Asp Leu Gly Ser Asn His Phe Asp Leu Asn
    130                 135                 140

Ile Pro Gly Gly Gly Val Gly Ile Phe Asp Gly Cys Thr Pro Gln Phe
145                 150                 155                 160

Gly Gly Leu Pro Gly Gln Arg Tyr Gly Gly Ile Ser Ser Arg Asn Glu
                165                 170                 175

Cys Asp Arg Phe Pro Asp Ala Leu Lys Pro Gly Cys Tyr Trp Arg Phe
            180                 185                 190

Asp Trp Phe Lys Asn Ala Asp Asn Pro Ser Phe Ser Phe Arg Gln Val
        195                 200                 205

Gln Cys Pro Ala Glu Leu Val Ala Arg Thr Gly Cys Arg Arg Asn Asp
    210                 215                 220

Asp Gly Asn Phe Pro Ala Val Gln Ile Pro Ser Ser Thr Ser Ser
225                 230                 235                 240

Pro Val Asn Gln Pro Thr Ser Thr Ser Thr Ser Thr Ser Thr Thr
                245                 250                 255

Ser Ser Pro Pro Val Gln Pro Thr Thr Pro Ser Gly Cys Thr Ala Glu
            260                 265                 270
```

| | | | | | | | | | | | | | | |
|---|---|---|---|---|---|---|---|---|---|---|---|---|---|---|
| Arg | Trp | Ala | Gln | Cys | Gly | Gly | Asn | Gly | Trp | Ser | Gly | Cys | Thr | Thr | Cys |
| | | 275 | | | | | 280 | | | | | 285 | | | |
| Val | Ala | Gly | Ser | Thr | Cys | Thr | Lys | Ile | Asn | Asp | Trp | Tyr | His | Gln | Cys |
| | | 290 | | | | | 295 | | | | | 300 | | | |
| Leu |
| 305 |

(2) INFORMATION FOR SEQ ID NO:3:

(i) SEQUENCE CHARACTERISTICS:
        (A) LENGTH: 1473 base pairs
        (B) TYPE: nucleic acid
        (C) STRANDEDNESS: unknown
        (D) TOPOLOGY: unknown (ix) FEATURE:
        (A) NAME/KEY: CDS
        (B) LOCATION: 97..1224

(xi) SEQUENCE DESCRIPTION: SEQ ID NO:3:

```
GAATTCGCGG CCGCTCATTC ACTTCATTCA TTCTTTAGAA TTACATACAC TCTCTTTCAA         60

AACAGTCACT CTTTAAACAA AACAACTTTT GCAACA ATG CGA TCT TAC ACT CTT         114
                                       Met Arg Ser Tyr Thr Leu
                                         1               5

CTC GCC CTG GCC GGC CCT CTC GCC GTG AGT GCT GCT TCT GGA AGC GGT         162
Leu Ala Leu Ala Gly Pro Leu Ala Val Ser Ala Ala Ser Gly Ser Gly
            10                  15                  20

CAC TCT ACT CGA TAC TGG GAT TGC TGC AAG CCT TCT TGC TCT TGG AGC         210
His Ser Thr Arg Tyr Trp Asp Cys Cys Lys Pro Ser Cys Ser Trp Ser
        25                  30                  35

GGA AAG GCT GCT GTC AAC GCC CCT GCT TTA ACT TGT GAT AAG AAC GAC         258
Gly Lys Ala Ala Val Asn Ala Pro Ala Leu Thr Cys Asp Lys Asn Asp
    40                  45                  50

AAC CCC ATT TCC AAC ACC AAT GCT GTC AAC GGT TGT GAG GGT GGT GGT         306
Asn Pro Ile Ser Asn Thr Asn Ala Val Asn Gly Cys Glu Gly Gly Gly
55                  60                  65                  70

TCT GCT TAT GCT TGC ACC AAC TAC TCT CCC TGG GCT GTC AAC GAT GAG         354
Ser Ala Tyr Ala Cys Thr Asn Tyr Ser Pro Trp Ala Val Asn Asp Glu
                75                  80                  85

CTT GCC TAC GGT TTC GCT GCT ACC AAG ATC TCC GGT GGC TCC GAG GCC         402
Leu Ala Tyr Gly Phe Ala Ala Thr Lys Ile Ser Gly Gly Ser Glu Ala
            90                  95                 100

AGC TGG TGC TGT GCT TGC TAT GCT TTG ACC TTC ACC ACT GGC CCC GTC         450
Ser Trp Cys Cys Ala Cys Tyr Ala Leu Thr Phe Thr Thr Gly Pro Val
        105                 110                 115

AAG GGC AAG AAG ATG ATC GTC CAG TCC ACC AAC ACT GGA GGT GAT CTC         498
Lys Gly Lys Lys Met Ile Val Gln Ser Thr Asn Thr Gly Gly Asp Leu
    120                 125                 130

GGC GAC AAC CAC TTC GAT CTC ATG ATG CCC GGC GGT GGT GTC GGT ATC         546
Gly Asp Asn His Phe Asp Leu Met Met Pro Gly Gly Gly Val Gly Ile
135                 140                 145                 150

TTC GAC GGC TGC ACC TCT GAG TTC GGC AAG GCT CTC GGC GGT GCC CAG         594
Phe Asp Gly Cys Thr Ser Glu Phe Gly Lys Ala Leu Gly Gly Ala Gln
                155                 160                 165

TAC GGC GGT ATC TCC TCC CGA AGC GAA TGT GAT AGC TAC CCC GAG CTT         642
Tyr Gly Gly Ile Ser Ser Arg Ser Glu Cys Asp Ser Tyr Pro Glu Leu
            170                 175                 180

CTC AAG GAC GGT TGC CAC TGG CGA TTC GAC TGG TTC GAG AAC GCC GAC         690
Leu Lys Asp Gly Cys His Trp Arg Phe Asp Trp Phe Glu Asn Ala Asp
        185                 190                 195

AAC CCT GAC TTC ACC TTT GAG CAG GTT CAG TGC CCC AAG GCT CTC CTC         738
```

|     |     |     |     |     |     |     |     |     |     |     |     |     |     |     |     |
|---|---|---|---|---|---|---|---|---|---|---|---|---|---|---|---|
| Asn | Pro | Asp | Phe | Thr | Phe | Glu | Gln | Val | Gln | Cys | Pro | Lys | Ala | Leu | Leu |
|     | 200 |     |     |     | 205 |     |     |     |     | 210 |     |     |     |     |     |

| GAC | ATC | AGT | GGA | TGC | AAG | CGT | GAT | GAC | GAC | TCC | AGC | TTC | CCT | GCC | TTC | 786 |
|---|---|---|---|---|---|---|---|---|---|---|---|---|---|---|---|---|
| Asp | Ile | Ser | Gly | Cys | Lys | Arg | Asp | Asp | Asp | Ser | Ser | Phe | Pro | Ala | Phe |  |
| 215 |  |  |  | 220 |  |  |  |  | 225 |  |  |  |  | 230 |  |  |

| AAG | GTT | GAT | ACC | TCG | GCC | AGC | AAG | CCC | CAG | CCC | TCC | AGC | TCC | GCT | AAG | 834 |
|---|---|---|---|---|---|---|---|---|---|---|---|---|---|---|---|---|
| Lys | Val | Asp | Thr | Ser | Ala | Ser | Lys | Pro | Gln | Pro | Ser | Ser | Ser | Ala | Lys |  |
|  |  |  |  | 235 |  |  |  |  | 240 |  |  |  |  | 245 |  |  |

| AAG | ACC | ACC | TCC | GCT | GCT | GCT | GCC | GCT | CAG | CCC | CAG | AAG | ACC | AAG | GAT | 882 |
|---|---|---|---|---|---|---|---|---|---|---|---|---|---|---|---|---|
| Lys | Thr | Thr | Ser | Ala | Ala | Ala | Ala | Ala | Gln | Pro | Gln | Lys | Thr | Lys | Asp |  |
|  |  |  | 250 |  |  |  |  |  | 255 |  |  |  | 260 |  |  |  |

| TCC | GCT | CCT | GTT | GTC | CAG | AAG | TCC | TCC | ACC | AAG | CCT | GCC | GCT | CAG | CCC | 930 |
|---|---|---|---|---|---|---|---|---|---|---|---|---|---|---|---|---|
| Ser | Ala | Pro | Val | Val | Gln | Lys | Ser | Ser | Thr | Lys | Pro | Ala | Ala | Gln | Pro |  |
|  |  | 265 |  |  |  |  | 270 |  |  |  |  | 275 |  |  |  |  |

| GAG | CCT | ACT | AAG | CCC | GCC | GAC | AAG | CCC | CAG | ACC | GAC | AAG | CCT | GTC | GCC | 978 |
|---|---|---|---|---|---|---|---|---|---|---|---|---|---|---|---|---|
| Glu | Pro | Thr | Lys | Pro | Ala | Asp | Lys | Pro | Gln | Thr | Asp | Lys | Pro | Val | Ala |  |
|  | 280 |  |  |  |  | 285 |  |  |  |  | 290 |  |  |  |  |  |

| ACC | AAG | CCT | GCT | GCT | ACC | AAG | CCC | GTC | CAA | CCT | GTC | AAC | AAG | CCC | AAG | 1026 |
|---|---|---|---|---|---|---|---|---|---|---|---|---|---|---|---|---|
| Thr | Lys | Pro | Ala | Ala | Thr | Lys | Pro | Val | Gln | Pro | Val | Asn | Lys | Pro | Lys |  |
| 295 |  |  |  |  | 300 |  |  |  |  | 305 |  |  |  |  | 310 |  |

| ACA | ACC | CAG | AAG | GTC | CGT | GGA | ACC | AAA | ACC | CGA | GGA | AGC | TGC | CCG | GCC | 1074 |
|---|---|---|---|---|---|---|---|---|---|---|---|---|---|---|---|---|
| Thr | Thr | Gln | Lys | Val | Arg | Gly | Thr | Lys | Thr | Arg | Gly | Ser | Cys | Pro | Ala |  |
|  |  |  |  | 315 |  |  |  |  | 320 |  |  |  |  | 325 |  |  |

| AAG | ACT | GAC | GCT | ACC | GCC | AAG | GCC | TCC | GTT | GTC | CCT | GCT | TAT | TAC | CAG | 1122 |
|---|---|---|---|---|---|---|---|---|---|---|---|---|---|---|---|---|
| Lys | Thr | Asp | Ala | Thr | Ala | Lys | Ala | Ser | Val | Val | Pro | Ala | Tyr | Tyr | Gln |  |
|  |  |  | 330 |  |  |  |  | 335 |  |  |  |  | 340 |  |  |  |

| TGT | GGT | GGT | TCC | AAG | TCC | GCT | TAT | CCC | AAC | GGC | AAC | CTC | GCT | TGC | GCT | 1170 |
|---|---|---|---|---|---|---|---|---|---|---|---|---|---|---|---|---|
| Cys | Gly | Gly | Ser | Lys | Ser | Ala | Tyr | Pro | Asn | Gly | Asn | Leu | Ala | Cys | Ala |  |
|  |  |  | 345 |  |  |  |  | 350 |  |  |  |  | 355 |  |  |  |

| ACT | GGA | AGC | AAG | TGT | GTC | AAG | CAG | AAC | GAG | TAC | TAC | TCC | CAG | TGT | GTC | 1218 |
|---|---|---|---|---|---|---|---|---|---|---|---|---|---|---|---|---|
| Thr | Gly | Ser | Lys | Cys | Val | Lys | Gln | Asn | Glu | Tyr | Tyr | Ser | Gln | Cys | Val |  |
|  |  | 360 |  |  |  |  | 365 |  |  |  |  | 370 |  |  |  |  |

| CCC | AAC | TAAATGGTAG | ATCCATCGGT | TGTGGAAGAG | ACTATGCGTC | TCAGAAGGGA | 1274 |
|---|---|---|---|---|---|---|---|
| Pro | Asn |  |  |  |  |  |  |
| 375 |  |  |  |  |  |  |  |

| TCCTCTCATG | AGCAGGCTTG | TCATTGTATA | GCATGGCATC | CTGGACCAAG | TGTTCGACCC | 1334 |
|---|---|---|---|---|---|---|
| TTGTTGTACA | TAGTATATCT | TCATTGTATA | TATTTAGACA | CATAGATAGC | CTCTTGTCAG | 1394 |
| CGACAACTGG | CTACAAAAGA | CTTGGCAGGC | TTGTTCAATA | TTGACACAGT | TTCCTCCATA | 1454 |
| AAAAAAAAAA | AAAAAAAA |  |  |  |  | 1473 |

( 2 ) INFORMATION FOR SEQ ID NO:4:

( i ) SEQUENCE CHARACTERISTICS:
    ( A ) LENGTH: 376 amino acids
    ( B ) TYPE: amino acid
    ( D ) TOPOLOGY: linear ( i i ) MOLECULE TYPE: protein ( x i ) SEQUENCE DESCRIPTION: SEQ ID NO:4:

| Met | Arg | Ser | Tyr | Thr | Leu | Leu | Ala | Leu | Ala | Gly | Pro | Leu | Ala | Val | Ser |
|---|---|---|---|---|---|---|---|---|---|---|---|---|---|---|---|
| 1 |  |  |  | 5 |  |  |  |  | 10 |  |  |  |  | 15 |  |

| Ala | Ala | Ser | Gly | Ser | Gly | His | Ser | Thr | Arg | Tyr | Trp | Asp | Cys | Cys | Lys |
|---|---|---|---|---|---|---|---|---|---|---|---|---|---|---|---|
|  |  |  | 20 |  |  |  |  | 25 |  |  |  |  | 30 |  |  |

| Pro | Ser | Cys | Ser | Trp | Ser | Gly | Lys | Ala | Ala | Val | Asn | Ala | Pro | Ala | Leu |
|---|---|---|---|---|---|---|---|---|---|---|---|---|---|---|---|
|  |  | 35 |  |  |  |  | 40 |  |  |  |  | 45 |  |  |  |

| Thr | Cys | Asp | Lys | Asn | Asp | Asn | Pro | Ile | Ser | Asn | Thr | Asn | Ala | Val | Asn |
|---|---|---|---|---|---|---|---|---|---|---|---|---|---|---|---|
|  | 50 |  |  |  |  | 55 |  |  |  |  | 60 |  |  |  |  |

| Gly | Cys | Glu | Gly | Gly | Gly | Ser | Ala | Tyr | Ala | Cys | Thr | Asn | Tyr | Ser | Pro |
|---|---|---|---|---|---|---|---|---|---|---|---|---|---|---|---|

```
  65                         70                          75                          80
Trp  Ala  Val  Asn  Asp  Glu  Leu  Ala  Tyr  Gly  Phe  Ala  Ala  Thr  Lys  Ile
                    85                        90                       95
Ser  Gly  Gly  Ser  Glu  Ala  Ser  Trp  Cys  Cys  Ala  Cys  Tyr  Ala  Leu  Thr
               100                      105                     110
Phe  Thr  Thr  Gly  Pro  Val  Lys  Gly  Lys  Lys  Met  Ile  Val  Gln  Ser  Thr
          115                      120                     125
Asn  Thr  Gly  Gly  Asp  Leu  Gly  Asp  Asn  His  Phe  Asp  Leu  Met  Met  Pro
     130                      135                     140
Gly  Gly  Gly  Val  Gly  Ile  Phe  Asp  Gly  Cys  Thr  Ser  Glu  Phe  Gly  Lys
145                      150                     155                          160
Ala  Leu  Gly  Gly  Ala  Gln  Tyr  Gly  Gly  Ile  Ser  Ser  Arg  Ser  Glu  Cys
               165                     170                          175
Asp  Ser  Tyr  Pro  Glu  Leu  Leu  Lys  Asp  Gly  Cys  His  Trp  Arg  Phe  Asp
               180                 185                     190
Trp  Phe  Glu  Asn  Ala  Asp  Asn  Pro  Asp  Phe  Thr  Phe  Glu  Gln  Val  Gln
          195                 200                     205
Cys  Pro  Lys  Ala  Leu  Leu  Asp  Ile  Ser  Gly  Cys  Lys  Arg  Asp  Asp  Asp
     210                 215                     220
Ser  Ser  Phe  Pro  Ala  Phe  Lys  Val  Asp  Thr  Ser  Ala  Ser  Lys  Pro  Gln
225                 230                     235                          240
Pro  Ser  Ser  Ser  Ala  Lys  Lys  Thr  Thr  Ser  Ala  Ala  Ala  Ala  Ala  Gln
               245                     250                     255
Pro  Gln  Lys  Thr  Lys  Asp  Ser  Ala  Pro  Val  Val  Gln  Lys  Ser  Ser  Thr
               260                     265                     270
Lys  Pro  Ala  Ala  Gln  Pro  Glu  Pro  Thr  Lys  Pro  Ala  Asp  Lys  Pro  Gln
          275                     280                     285
Thr  Asp  Lys  Pro  Val  Ala  Thr  Lys  Pro  Ala  Ala  Thr  Lys  Pro  Val  Gln
     290                     295                     300
Pro  Val  Asn  Lys  Pro  Lys  Thr  Thr  Gln  Lys  Val  Arg  Gly  Thr  Lys  Thr
305                     310                     315                          320
Arg  Gly  Ser  Cys  Pro  Ala  Lys  Thr  Asp  Ala  Thr  Ala  Lys  Ala  Ser  Val
               325                          330                     335
Val  Pro  Ala  Tyr  Tyr  Gln  Cys  Gly  Gly  Ser  Lys  Ser  Ala  Tyr  Pro  Asn
               340                     345                     350
Gly  Asn  Leu  Ala  Cys  Ala  Thr  Gly  Ser  Lys  Cys  Val  Lys  Gln  Asn  Glu
          355                     360                     365
Tyr  Tyr  Ser  Gln  Cys  Val  Pro  Asn
     370                     375
```

DYE TRANSFER INHIBITING COMPOSITIONS

FIELD OF THE INVENTION

The present invention relates to an enzymatic composition for inhibiting the transfer of dye from a dyed fabric to another fabric during washing.

BACKGROUND OF THE INVENTION

One of the most persistent and troublesome problems arising during modern fabric laundering operations is the tendency of some colored fabrics to release dye into the laundering solutions. The dye is then transferred onto other fabrics being washed therewith.

One way of overcoming this problem would be to bleach the fugitive dyes washed out of dyed fabrics before they have the opportunity to become attached to other articles in the wash.

Suspended or solubilized dyes can to some degree be oxidized in solution by employing known bleaching agents.

GB 2 101 167 describes a stable liquid bleaching composition containing a hydrogen peroxide precursor which is activated to yield hydrogen peroxide on dilution.

However, it is important at the same time not to bleach the dyes actually remaining on the fabrics, that is, not to cause color damage.

U.S. Pat. No. 4,077,768 describes a process for inhibiting dye transfer by the use of an oxidizing bleaching agent together with catalytic compounds such as iron porphins.

U.S. patent application Ser. No. 07/421,414 now abandoned describes peroxidases and oxidases utilized for the oxidation of organic or inorganic substances, including coloured substances. A dye transfer inhibiting composition comprising an enzymatic system capable of generating hydrogen peroxide and iron catalysts has been disclosed in copending EP Patent Application 91202655.6 filed Oct. 9, 1991.

EP 424 398-A describes a detergent additive capable of exerting a bleaching effect comprising a peroxidase. The additive further comprises one or more enzymes, particularly a lipase, protease, amylase or a cellulase.

EP-A-350 098 discloses a C14CMC-method which defines a cellulase selection criteria relevant for detergent application. A minimum of 10% removal of immobilized radioactive labelled carboxymethylcellulose according to the CMC-method at $25 \times 10^{-6}\%$ by weight of the cellulase protein in the test solution has been found to provide high active cellulase.

A preferred group of cellulase falling under the high activity definition according to the present invention has been disclosed in copending Danish Patent Application No. 1159/90 filed May 5, 1990. There is disclosed a cellulase preparation consisting essentially of a homogeneous endoglucanase component which is immunoreactive with a monoclonal antibody raised against a partially purified=43 kD cellulase derived from *Humicola insolens* DM1800.

It has now been surprisingly found that the efficiency of peroxidases in terms of dye transfer inhibition, is considerably enhanced by using said high activity cellulase and more in particular the specific cellulase preparation disclosed in copending Danish Patent Application No. 1159/90. It is therefore an object of the present invention to provide dye transfer inhibiting compositions which exhibit optimum dye transfer in wash liquids by using said high activity cellulase and peroxidase.

According to one embodiment of this invention a dye transfer inhibiting composition is provided which comprises a cost-effective cellulase preparation, e.g. by employing recombinant DNA techniques.

According to another embodiment of this invention a process is also provided for laundering operations involving colored fabrics.

SUMMARY OF THE INVENTION

The present invention provides a dye transfer inhibiting composition comprising an enzyme exhibiting peroxidase activity, a hydrogen peroxide or a hydrogen peroxide precursor or an enzymatic system capable of generating hydrogen peroxide, an additional oxidizable substrate, and a cellulase, characterized in that the cellulase provides at least 10% removal of immobilized radioactive labelled carboxymethyl cellulose according to C14CMC method at $25 \times 10^{-6}\%$ by weight of the laundry test solution.

According to the present invention, a preferred cellulase consists essentially of a homogeneous endoglucanase component which is immunoreactive with a monoclonal antibody raised against a partially purified=43 kD cellulase derived from *Humicola insolens* DM1800.

DETAILED DESCRIPTION OF THE INVENTION

Cellulase

The activity of enzymes and particularly the activity of cellulase enzyme has been defined for various applications by different analytical methods. These methods all attempt to provide a realistic assessment of the expected in use performance or at least a measurement correlating with the in use performance. As has been detailed in European Patent Application EP-A-350098, many of the methods, particularly these frequently used by cellulase manufacturers, are not sufficiently correlated with the in use performance of cellulase in laundry detergent compositions. This is due to the various other usage conditions for which these activity measurement methods have been developed.

The method described in EP-A-350098, has been developed to be and to have a predictive correlation for the ranking of cellulase activity in laundry detergent compositions.

The present invention therefore uses the method disclosed in EP-A-350098 to screen cellulases in order to distinguish cellulases which are useful in the present invention and those which would not provide the objectives of the present invention. The screening method, hereinafter referred to as C14CMC-Method, which has been adopted from the method disclosed in EP-A-350098, can be described as follows:
Principle The principle of the C14CMC-Method for screening is to measure at a defined cellulase concentration in a wash solution the removal of immobilized carboxy methyl cellulose (CMC) from a cloth substrate. The removal of CMC is measured by radio-active labelling of some of the CMC by using C14 radio-active carbon. Simple counting of the amount of radio-active C14 on the cloth substrate before and after the cellulase treatment allows the evaluation of the cellulase activity.

Sample Preparation

CMC preparation: The radio-active CMC stock solution is prepared according to Table I. The radio-active CMC can be obtained by methods referred to in EP-A-350098.

Fabric substrates: The fabric substrates are muslin cotton swatches having a size of 5 cm×5 cm. They are inocculated with 0.35 ml of the radio-active labelled CMC stock solution in their center. The muslin cotton swatches are then airdried.

Immobilization of CMC: To immobilize the radio-active labelled CMC on the muslin cotton swatches, laundero-meter equipment "Linitest Original Haunau" made by Original Haunau, Germany, is used. A metal jar of the laundero-meter is filled with 400 ml of hard water (4 mmol/liter of $Ca^{++}$ ions). A maximum number of 13 swatches can be used per jar. The jar is then incubated in a heat-up cycle from 20° C. to 60° C. over 40 minutes in the laundero-meter equipment. After incubation the swatches are rinsed under running city water for 1 minute. They are squeezed and allowed to airdry for at least 30 minutes. According to EP-A-350098 samples of the swatches with immobilized radio-active CMC can also be measured as "blank samples" without washing.

Sample Treatment

Laundry test solution: The laundry test solution is prepared according to the composition of Table II. It is balanced to pH 7.5. The laundry test solution is the basis to which a cellulase test sample is added. Care should be taken to not dilute the laundry test solution by adding water to a 100% balance prior to having determined the amount of cellulase to be added. The amount of cellulase which is used in this screening test should be added to provide $25 \times 10^{-6}$ weight percent of cellulase protein in the laundry test solution (equivalent to 0.25 milligram/liter at 14.5° C.).

Wash procedure: The swatches thus inocculated with radio-active labelled CMC are then treated in a laundry simulation process. The laundry process is simulated in the laundero-meter type equipment, "Linitest, Original Haunau", by Original Haunau, Haunau Germany An individual swatch is put into a 20 $cm^3$ glass vial. The vial is filled with 10 ml of the laundry test solution and then sealed liquid tight. Up to 5 vials are put into each laundero-meter jar. The jar is filled with water as a heat tranfer medium for the laundering simulation. The laundering simulation is conducted as a heat-up cycle from 20° C. to 60° C. over 40 minutes.

After the processing of the samples the vials are submerged in cold water and subsequently each swatch is taken out of its vial, rinsed in a beaker under running soft water, squeezed and allowed to airdry for at least 30 minutes.

Measurement

In order to measure radio-active labelled CMC removal, a scintillation counter, for example, a LKB 1210 Ultrabeta Scintillation Counter, is used. In order to obtain most accurate results, the instruction manual for optimum operation of the particular scintillation counter should be followed. For example, for the LKB 1210 Ultrabeta Scintillation Counter, the following procedure should be followed. The swatch to be measured is put into a plastic vial filled with 12 ml of scintillator liquid (e.g. scintillator 299 from Packard). The swatch is then allowed to stabilize for at least 30 minutes. The vial is then put into the LKB 1210 Ultrabeta Scintillation Counter and the respective radio-activity counts for the swatch is obtained.

In order to measure the amount of CMC removal due only to the cellulase, a measurement of a swatch which has been inocculated at the same time but has been treated in the laundry test solution without cellulase, is necessary. The activity of the cellulase is then expressed as percent of radio-active labelled CMC removal. This percentage is calculated by the following formula:

$$\% \text{ of radio-active CMC removal} = \frac{XO - XC}{XO} \times 100$$

Wherein

XO is the radioactivity scintillation count of a swatch treated with the laundry test solution without cellulase XC is the radioactivity scintillation count of a swatch treated with the laundry test solution containing the cellulase to be evaluated Statistical Considerations, Procedure Confirmation In order to provide statistically sound results, standard statistical analysis should be employed. For the given example, using the LKB 1210 Ultrabeta Scintillation Counter, it has been found that a sample size of 3 swatches for each radioactivity scintillation count can be used.

In order to confirm the procedure by internal crosschecking, measurement and calculation of the "blank sample" according to EP-A-350098 are recommended. This will allow to detect and eliminate errors.

Interpretation of Results

The described screening test does provide a fast, unique and reliable method to identify cellulases which satisfy the activity criteria of the present invention versus cellulases which are not part of the present invention.

It has been found that a removal of 10% or more of the immobilized radioactive labelled CMC according to the above C14CMC-method, indicates that the respective cellulase satisfies the requirements of the invention.

It will be obvious to those skilled in the art that removal percentages above 10% indicate a higher activity for the respective cellulase. It therefore is contemplated that cellulase providing above 25% or preferably above 50% removal of radioactive labelled CMC, at the protein concentration in the laundry test solution according to the C14CMC-method, would provide indication of an even better performance of the cellulase for use in laundry detergents.

It also has been contemplated that usage of higher concentrations of cellulase for C14CMC-method, would provide higher removal percentages. However, there exists no linear proven correlation between cellulase concentration and removal percentage obtained by it.

It also has been contemplated that usage of higher concentrations of cellulase for C14CMC-method, would provide higher removal percentages.

TABLE I

| Radioactive $C_{14}$ labelled CMC stock solution (all percentages by weight of total solution) | |
|---|---|
| Total CMC* (CMC should be detergent grade CMC with a degree of substitution from about 0.47 to about 0.7) | $99.2 \times 10^{-3}\%$ |
| Ethanol | $14985.12 \times 10^{-3}\%$ |
| Deionized Water | $84915.68 \times 10^{-3}\%$ |
| Total: | 100% |

*Total CMC contains non-radioactive and radio-active CMC to provide a radio-activity which allows sufficiently clear readings on the scintillation counter used. For example, the radio-active CMC can have an activity of 0.7 millicurie/g and be mixed with non-radioactive CMC at a ratio of 1:6.7.

TABLE II

| Laundry test solution (all percentages by weight of total solution) | |
| --- | --- |
| Linear $C_{12}$ alkyl benzene sulphonic acid | 0.110% |
| Coconut alkyl sulphate (TEA salt) | 0.040% |
| $C_{12-15}$ alcohol ethoxylate (E07) | 0.100% |
| Coconut fatty acid | 0.100% |
| Oleic acid | 0.050% |
| Citric acid | 0.010% |
| Triethanolamine | 0.040% |
| Ethanol | 0.060% |
| Propanediol | 0.015% |
| Sodium hydroxide | 0.030% |
| Sodium formate | 0.010% |
| Protease | 0.006% |
| Water (2.5 mmol/liter $Ca^{++}$), pH adjustment agent (HCL or NaOH solutions) and cellulose | balance to 100% |

According to the present invention, preferred cellulases are those as described in Danish Patent Application 1159/90. For example, a cellulase preparation useful in the compositions of the invention can consist essentially of a homogeneous endoglucanase component, which is immunoreactive with an antibody raised against a highly purified 43 kD cellulase derived from *Humicola insolens*, DSM 1800, or which is homologous to said 43 kD endoglucanase.

It should be stressed that all cellulase enzymes according to the present invention have to meet the criteria of the above mentioned screening test. However, in the Danish Patent Application 1159/90 additional criteria are established allowing to identify preferred cellulase enzymes in combination with present screening test.

Cellulase preparations particulary useful in the compositions of the invention are those in which in addition to the screening test, the endoglucanase component exhibits a CMC-endoase activity of at least about 50, preferably at least about 60, in particular at least about 90 CMC-endoase units per mg of total protein. In particular, a preferred endoglucanase component exhibits a CMC-endoase activity of at least 100 CMC-endoase units per mg of total protein.

In the present context, the term "CMC-endoase activity" (cevu) refers to the endoglucanase activity of the endoglucanase component in terms of its ability to degrade cellulose to glucose, cellobiose and triose, as determined by a viscosity decrease of a solution of carboxymethyl cellulose (CMC) after incubation with the cellulase preparation of the invention, as described in detail below.

The CMC-endoase (endoglucanase) activity can be determined from the viscosity decrease of CMC, as follows: A substrate solution is prepared, containing 35 g/l CMC (Hercules 7 LFD) in 0.1M tris buffer at pH 9.0. The enzyme sample to be analyzed is dissolved in the same buffer. 10 ml substrate solution and 0.5 ml enzyme solution are mixed and transferred to a viscosimeter (e.g. Haake VT 181, NV sensor, 181 rpm), thermostated at 40° C. Viscosity readings are taken as soon as possible after mixing and again 30 minutes later. The amount of enzyme that reduces the viscosity to one half under these conditions is defined as 1 unit of CMC-endoase activity.

SDS polyacrylamide gel electrophoresis (SDS-PAGE) and isoelectric focusing with marker proteins in a manner known to persons skilled in the art were used to determine the molecular weight and isoelectric point (pI), respectively, of the endoglucanase component in the cellulase preparation useful in the present context. In this way, the molecular weight of a specific endoglucanase component was determined to be 43 kD. The isoelectric point of this endoglucanase was determined to be about 5.1.

The cellobiohydrolase activity may be defined as the activity towards cellobiose p-nitrophenyl. The activity is determined as μmole nitrophenyl released per minute at 37° C. and pH 7.0. The present endoglucanase component was found to have essentially no cellobiohydrolase activity.

The endoglucanase component in the cellulase preparation herein has initially been isolated by extensive purification procedures, i.a. involving reverse phase HPLC purification of a crude *H. insolens* cellulase mixture according to U.S. Pat. No. 4,435,307. This procedure has surprisingly resulted in the isolation of a 43 kD endoglucanase as a single component with unexpectedly favourable properties due to a surprisingly high endoglucanase activity.

Also, in addition to the screening test, the cellulase enzymes useful in the present compositions can further be defined as enzymes exhibiting endoglucanase activity (in the following referred to as an "endoglucanase enzyme"), which enzymes have the amino acid sequence shown in SEQ ID NO: 2, or a homologue thereof exhibiting endoglucanase activity.

In the present context, the term "homologue" is intended to indicate a polypeptide encoded by DNA which hybridizes to the same probe as the DNA coding for the endoglucanase enzyme with this amino acid sequence under certain specified conditions (such as presoaking in 5×SSC and prehybridizing for 1 h at 40° C. in a solution of 20% formamide, 5×Denhardt's solution, 50 mM sodium phosphate, pH 6.8, and 50 ug of denatured sonicated calf thymus DNA, followed by hybridization in the same solution supplemented with 100 μM ATP for 18 h at 40° C.). The term is intended to include derivatives of the aforementioned sequence obtained by addition of one or more amino acid residues to either or both the C- and N-terminal of the native sequence, substitution of one or more amino acid residues at one or more sites in the native sequence, deletion of one or more amino acid residues at either or both ends of the native amino acid sequence or at one or more sites within the native sequence, or insertion of one or more amino acid residues at one or more sites in the native sequence.

The endoglucanase enzyme herein may be one producible by species of Humicola such as *Humicola insolens* e.g. strain DSM 1800, deposited on Oct. 1, 1981 at the Deutsche Sammlung yon Mikroorganismen, Mascheroder Weg 1B, D-3300 Braunschweig, FRG, in accordance with the provisions of the Budapest Treaty on the International Recognition of the Deposit of Microorganisms for the Purposes of Patent Procedure (the Budapest Treaty).

In still a further aspect, the cellulase enzymes useful herein can be defined, in addition to the screening test, as endoglucanase enzymes which have the amino acid sequence shown in SEQ ID NO: 4, or a homologue thereof (as defined above) exhibiting endoglucanase activity. Said endoglucanase enzyme may be one producible by a species of Fusarium, such as *Fusarium oxysporum*, e.g. strain DSM 2672, deposited on Jun. 6, 1983 at the Deutsche Sammlung von Mikroorganismen, Mascheroder Weg 1B, D-3300 Braunschweig, FRG, in accordance with the provisions of the Budapest Treaty.

Furthermore, it is contemplated that homologous endoglucanases may be derived from other microorganisms producing cellulolytic enzymes, e.g. species of Trichoderma, Myceliophthora, Phanerochaete, Schizophyllum, Penicillium, Aspergillus, and Geotricum.

For industrial production of the cellulase preparation herein, however, it is preferred to employ recombinant DNA techniques or other techniques involving adjustements of fermentations or mutation of the microorganisms involved to ensure overproduction of the desired enzymatic activities. Such methods and techniques are known in the art and may readily be carried out by persons skilled in the art.

The endoglucanase component may thus be one which is producible by a method comprising cultivating a host cell transformed with a recombinant DNA vector which carries a DNA sequence encoding said endoglucanase component or a precursor of said endoglucanase component as well as DNA sequences encoding functions permitting the expression of the DNA sequence encoding the endoglucanase component or precursor thereof, in a culture medium under conditions permitting the expression of the endoglucanase component or precursor thereof and recovering the endoglucanase component from the culture.

DNA constructs comprising a DNA sequence encoding an endoglucanase enzyme as described above, or a precursor form of the enzyme, include the DNA constructs having a DNA sequence as shown in SEQ ID NO: 1 or SEQ ID. NO: 3, or a modification thereof. Examples of suitable mofidications of the DNA sequence are nucleotide substitutions which do not give rise to another amino acid sequence of the endoglucanase, but which correspond to the codon usage of the host organism into which the DNA construct is introduced or nucleotide substitutions which do give rise to a different amino acid sequence and therefore, possibly, a different protein structure which might give rise to an endoglucanase mutant with different properties than the native enzyme. Other examples of possible modifications are insertion of one or more nucleotides at either end of the sequence, or deletion of one or more nucleotides at either end or within the sequence.

DNA constructs encoding endoglucanase enzymes useful herein may be prepared synthetically by established standard methods, e.g. the phosphoamidite method described by S. L. Beaucage and M. H. Caruthers, *Tetrahedron Letters* 22, 1981, pp. 1859–1869, or the method described by Matthes et al., *EMBO Journal* 3, 1984, pp. 801–805. According to the phosphoamidite method, oligonucleotides are synthesized, e.g. in an automatic DNA synthesizer, purified, annealed, ligated and cloned in suitable vectors.

A DNA construct encoding the endoglucanase enzyme or a precursor thereof may, for instance, be isolated by establishing a cDNA or genomic library of a cellulase-producing microorganism, such as *Humicola insolens,* DSM 1800, and screening for positive clones by conventional procedures such as by hybridization using oligonucleotide probes synthesized on the basis of the full or partial amino acid sequence of the endoglucanase in accordance with standard techniques (cf. Sambrook et al., *Molecular Cloning: A Laboratory Manual,* 2nd. Ed. Cold Spring Harbor, 1989), or by selecting for clones expressing the appropriate enzyme activity (i.e. CMC-endoase activity as defined above), or by selecting for clones producing a protein which is reactive with an antibody against a native cellulase (endoglucanase).

Finally, the DNA construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire DNA construct, in accordance with standard techniques. The DNA construct may also be prepared by polymerase chain reaction using specific primers, for instance as described in U.S. Pat. No. 4,683,202 or R. K. Saiki et al., *Science* 239, 1988, pp. 487–491.

Recombinant expression vectors into which the above DNA constructs are inserted include any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into wich it has been integrated.

In the vector, the DNA sequence encoding the endoglucanase should be operably connected to a suitable promoter and terminator sequence. The promoter may be any DNA sequence which shows transcriptional activity in the host cell of choice and may be derived from genes encoding proteins either homologous or heterologous to the host cell. The procedures used to ligate the DNA sequences coding for the endoglucanase, the promoter and the terminator, respectively, and to insert them into suitable vectors are well known to persons skilled in the art (cf., for instance, Sambrook et al., op.cit.).

Host cells which are transformed with the above DNA constructs or the above expression vectors may be for instance belong to a species of Aspergillus, most preferably *Aspergillys oryzae* or *Aspergillus niger*. Fungal cells may be transformed by a process involving protoplast formation and transformation of the protoplasts followed by regeneration of the cell wall in a manner known per se. The use of Aspergillus as a host microorganism is described in EP 238 023 (of Novo Industri A/S), the contents of which are hereby incorporated by reference. The host cell may also be a yeast cell, e.g. a strain of *Saccharomyces cerevisiae.*

Alternatively, the host organism may be a bacterium, in particular strains of Streptomyces and Bacillus, and *E. coli.* The transformation of bacterial cells may be performed according to conventional methods, e.g. as described in Sambrook et al., *Molecular Cloning: A Laboratory Manual,* Cold Spring Harbor, 1989.

The screening of appropriate DNA sequences and construction of vectors may also be carried out by standard procedures, cf. Sambrook et al., op.cot.

The medium used to cultivate the transformed host cells may be any conventional medium suitable for growing the host cells in question. The expressed endoglucanase may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

By employing recombinant DNA techniques as indicated above, techniques of protein purification, techniques of fermentation and mutation or other techniques which are well known in the art, it is possible to provide endoglucanases of a high purity.

The level in the present composition of cellulase described above should be such that the amount of enzyme protein to be delivered in the wash solution is from 0.005 to 40 mg/liter of wash solution, preferably 0.01 to 10 mg/liter of wash solution.

Peroxidases

The peroxidases which may be employed for the present purpose may be isolated from and are producible by plants (e.g. horseradish peroxidase) or micoorganisms such as fungi or bacteria. Some preferred fungi include strains belonging to the subdivision Deuteromycotina, class Hyphomycetes, e.g. Fusarium, Humicola, Tricoderma, Myrothecium, Verticillum, Arthromyces, Caldariomyces, Ulocladium, Embellisia, Cladosporium or Dreschlera, in particular *Fusarium oxysporum* (DSM 2672), *Humicola insolens*, *Trichoderma resii*, *Myrothecium verrucana* (IFO 6113), *Verticilluum alboatrum*, *Verticillum dahlie*, *Arthromyces ramosus* (FERM P-7754), *Caldariomyces fumago*, *Ulocladium chartarum*, *Embellisia allior Dreschlera halodes*.

Other preferred fungi inlclude strains belonging to the subdivision Basidiomycotina, class Basidiomycetes, e.g. Coprinus, Phanerochaete, Coriolus or Trametes, in particular *Coprinus cinereus f. microsporus* (IFO 8371), *Coprinus macrorhizus*, *Phanerochaete chrysosporium* (e.g. NA-12) or *Coriolus versicolor* (e.g. PR4 28-A).

Further preferred fungi include strains belonging to the subdivision Zygomycotina, class Mycoraceae, e.g. Rhizopus or Mucor, in particular *Mucor hiemalis*.

Some preferred bacteria include strains of the order Actinomycetales, e.g. *Streptomyces spheroides* (ATTC 23965), *Streptomyces thermoviolaceus* (IFO 12382) or *Streptoverticillum verticillium ssp. verticillium*.

Other preferred bacteria inlude *Bacillus pumillus* (ATCC 12905), *Bacillus stearothermophilus*, *Rhododbacter sphaeroides*, *Rhodomonas palustri*, *Streptococcus lactis*, *Pseudomonas purrocinia* (ATCC 15958) or *Pseudomonas fluorescens* (NRRL B-11).

Other potential sources of useful peroxidases are listed in B. C. Saunders et al., op. cit., pp. 41–43.

Methods of producing enzymes to be used according to the invention are described in the art, cf. for example *FEBS Letters* 1625, 173(1), *Applied and Environmental Microbiology*, February 1985, pp. 273–278, *Applied Microbiol. Biotechnol.* 26, 1987, pp. 158–163, *Biotechnology Letters* 9(5), 1987, pp. 357–360, *Nature* 326, 2 Apr. 1987, *FEBS Letters* 4270, 209(2), p. 321, EP 179 486, EP 200 565, GB 2 167 421, EP 171 074, and *Agric. Biol. Chem.* 50(1), 1986, p. 247.

Particularly preferred peroxidases are those which are active at the typical pH of washing liquors, i.e. at a pH of 6.5–10.5, preferably 6.5–9.5, and most preferably 7.5–9.5. Such enzymes may be isolated by screening for the relevant enzyme production by alkalophilic microorganisms, e.g. using the ABTS assay described in R. E. Childs and W. G. Bardsley, *Biochem. J.* 145, 1975, pp. 93–103.

Other preferred peroxidases are those which exhibit a good thermostability as well as a good stability towards commonly used detergent components such as non-ionic, cationic, or anionic surfactants, detergent builders, phosphate etc.

Another group of useful peroxidases are haloperoxidases, such as chloro- and bromoperoxidases.

The peroxidase-enzyme may futhermore be one which is producible by a method comprising cultivating a host cell transformed with a recombinant DNA vector which carries a DNA sequence encoding said enzyme as well as DNA sequences encoding functions permitting the expression of the DNA sequence encoding the enzyme, in a culture medium under conditions permitting the expression of the enzyme and recovering the enzyme from the culture.

A DNA fragment encoding the enzyme may, for instance, be isolated by establishing a cDNA or genomic library of a microorganism producing the enzyme of interest, such as one of the organisms mentioned above, and screening for positive clones by conventional procedures such as by hybridization to oligonucleotide probes synthesized on the basis of the full or partial amino acid sequence of the enzyme, or by selecting for clones expressing the appropriate enzyme activity, or by selecting for clones producing a protein which is reactive with an antibody against the native enzyme.

Once selected, the DNA sequence may be inserted into a suitable replicable expression vector comprising appropriate promotor, operator and terminator sequences permitting the enzyme to be expressed in a particular host organism, as well as an origin of replication, enabling the vector to replicate in the host organism in question.

The resulting expression vector may then be transformed into a suitable host cell, such as a fungal cell, preferred examples of which are a species of Aspergillus, most preferably *Aspergillus oryzae* or *Aspergillus niger*. Fungal cells may be transformed by a process involving protoplast formation and transformation of the protoplasts followed by regeneration of the cell wall in a manner known per se. The use of Aspergillus as a host micoorganism is described in EP 238,023 (of Novo Industri A/S), the contents of which are hereby incorporated by reference.

Alternatively, the host organisms may be a bacterium, in particular strains of Streptomyces and Bacillus, or *E. coli*. The transformation of bacterial cells may be performed according to conventional methods, e.g. as described in T. Maniatis et al., *Molecular Cloning: A Laboratory Manual*, Cold Spring Harbor, 1982.

The screening of appropriate DNA sequences and construction of vectors may also be carried out by standard procedures, cf. T. Maniatis et al., op. cit.

The medium used to cultivate the transformed host cells may be any conventional medium suitable for growing the host cells in question. The expressed enzyme may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

The screening of appropriate DNA sequences and construction of vectors may also be carried out by standard procedures, cf. T. Maniatis et al., op. cit.

The medium used to cultivate the transformed host cells may be any conventional medium suitable for growing the host cells in question. The expressed enzyme may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

At the beginning or during the process, $H_2O_2$ may be added, e.g. in an amount of 0.001–5 mM, particularly 0.01–1 mM. When using *Coprinus peroxidase*, 0.01–0.25 mM $H_2O_2$ is preferred, and with *B. pumilus peroxidase* 0.1–1 mM $H_2O_2$.

The hydrogen peroxide may be added as hydrogen peroxide or a precursor thereof, preferably a perborate or percarbonate. The level of hydrogen peroxide precursor that can be used is dependent on the specific properties of the peroxidase chosen, e.g. *Coprinus peroxidase* should be applied in a detergent composition which contains less than 5% perborate.

In the process of this invention, it may be desirable to utilize an enzymatic process for hydrogen peroxide formation. Thus, the process according to the invention may additionally comprise adding an enzymatic system (i.e. an enzyme and a substrate therefor) which is capable of generating hydrogen peroxide at the beginning or during the washing and/or rinsing process.

One such category of hydrogen peroxide generating systems comprises enzymes which are able to convert molecular oxygen and an organic or inorganic substrate into hydrogen peroxide and the oxidized substrate respectively. These enzymes produce only low levels of hydrogen peroxide, but they may be employed to great advantage in the process of the invention as the presence of peroxidase ensures an efficient utilization of the hydrogen peroxide produced.

Preferred hydrogen peroxide-generating enzymes are those which act on cheap and readily available substrates which may conveniently be included into detergent compositions. An example of such a substrate is glucose which may be utilized for hydrogen peroxide production by means of glucose oxidase. Suitable oxidases include those which act on aromatic compounds such as phenols and related substances, e.g. catechol oxidases, laccase. Other suitable oxidases are urate oxidase, galactose oxidase, alcohol oxidases, amine oxidases, amino acid oxidase, amyloglucosidase, and cholesterol oxidase.

The preferred enzymatic systems are alcohol and aldehyde oxidases.

The more preferred systems for granular detergent application would have solid alcohols, e.g. glucose whose oxidation is catalysed by glucose oxidase to glucoronic acid with the formation of hydrogen peroxide.

The more preferred systems for liquid detergent application would involve liquid alcohols which could also act as, for example, solvents. An example is ethanol/ethanol oxidase.

The quantity of oxidase to be employed in compositions according to the invention should be at least sufficient to provide a constant generation of 0.01 to 10 ppm AvO per minute in the wash. For example, with the glucose oxidase, this can be achieved at room temperature and at pH 6 to 11, preferentially 7 to 9 with 50–5000 U/l glucose oxidase, 0.005 to 0.5% glucose under constant aeration.

The addition of another oxidisable substrate for the peroxidase at the beginning or during the washing and/or rinsing process may enhance the dye transfer inhibitory effect of the peroxidase employed. This is thought to be ascribable to the formation of short-lived radicals or other oxidised states of this substrate which participate in the bleaching or other modification of the coloured substance. Examples of such oxidisable substrates are metal ions, e.g. $Mn^{++}$, halide ions, e.g. chloride or bromide ions, or organic compounds such as phenols, e.g. p-hydroxycinnamic acid or 2,4-dichlorophenol. Other examples of phenolic compounds which may be used for the present purpose are those given in M. Kato and S. Shimizu, *Plant Cell Physiol.* 26(7), 1985, pp. 1291–1301 (cf. Table 1 in particular) or B. C. Saunders et al., op. cit., p. 141 ff. The amount of oxidisable substrate to be added is suitably between about 1 µM and 1 mM.

In the process of the invention, the peroxidase will typically be added as a component of a detergent composition and may be added in an amount of 0.01–100 mg enzyme per liter of wash liquid. As such, it may be included in the detergent composition in the form of a non-dusting granulate, a liquid, in particular a stabilized liquid, or a protected enzyme. Non-dusting granulates may be produced, e.g. as disclosed in U.S. Pat. Nos. 4,106,991 and 4,661,452 (both to Novo Industri A/S) and may optionally be coated by methods known in the art. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238,216. The detergent composition may also comprise one or more substrates for the peroxidase. Usually, the pH of a solution of the detergent composition of the invention will be preferably from 7–12, especially from 7.5 to 9.5. The wash pH is dependent on the peroxidase chosen, e.g. Coprinus peroxidase should be applied in a wash pH below 9.5.

Detergent Adjuncts

The composition of the present can contain the usual components of such detergent compositions in the usual amounts. Thus, organic surfactants anionic, nonionic, ampholytic, or zwitterionic or less usually cationic and mixtures thereof, may be present. Suitable surfactants are well known in the art and an extensive list of such compounds is given in U.S. Pat. No. 3,717,630 and in U.S. patent application Ser. No. 589,116.

Detergent compositions useful in the present invention contain from 1 to 95%, preferable from 5 to 40% of a nonionic, anionic, zwitterionic, or mixtures thereof. Detergency builders, whether inorganic or organic, phosphatic or not, water-soluble or insoluble, and other water-soluble salts may be present, and salts of this sort may be employed whether organic detergents are present or not. A description of suitable builders is given in U.S. Pat. No. 3,936,537 and in U.S. patent application Ser. No. 589,116. Detergent builders are present from 0 to 50%, preferably from 5 to 40%.

Other components used in detergent compositions may be employed, such as suds boosting or depressing agents, enzymes and stabilizers or activators, soil-suspending agents soil-release agents, optical brighteners, abrasives, bactericides, tarnish inhibitors, coloring agents, and perfumes.

These components, particularly the enzymes, optical brighteners, coloring agents, and perfumes, should preferably be chosen such that they are compatible with the bleach component of the composition.

The detergent compositions according to the invention can be in liquid, paste or granular forms. The enzyme may be formulated in any convenient form, e.g. as a powder or liquid. The enzyme may be stabilized in a liquid by inclusion of enzyme stabilizers. Liquid deterents may further include stabilized hydrogen peroxide precursors. Granular compositions according to the present invention can also be in "compact form", i.e. they may have a relatively higher density than conventional granular detergents, i.e. from 550 to 950 g/l; in such case, the granular detergent compositions according to the present invention will contain a lower amount of "inorganic filler salt", compared to conventional granular detergents; typical filler salts are alkaline earth metal salts of sulphates and chlorides, typically sodium sulphate; "compact" detergents typically comprise not more than 10% filler salt.

The present invention also relates to a process for inhibiting dye transfer from one fabric to another of solubilized and suspended dyes encountered during fabric laundering operations involving colored fabrics.

The process comprises contacting fabrics with a laundering solution as hereinbefore described.

The process of the invention is conveniently carried out in the course of the washing process. The washing process is preferably carried out at 5° C. to 75° C., especially 20° C. to 60° C. The pH of the treatment solution is preferably from 7 to 12, especially from 7 to 9.5.

The process and compositions of the invention can also be used as additive during laundry operations.

The following examples illustrate the present invention and the unexpected superior colour care benefits obtained therefrom.

EXAMPLE I

Criticality of the Cellulase Performance Parameter of Claim 1

The following test was conducted:
Test Conditions
  washing temperature: 60° C. (heat up cycle)
  Washing time: 40 min.
  pH=7.5
  Water hardness: 4 mmol/L
  Detergent concentration: 1%
  Detergent composition: crf. EPA 350 098 ex. 1
  Cellulases:
    1) Celluzyme® supplied by Novo Nordisk=reference
    2) 43 kD endoglucanase=cellulase according to the invention
Test Results

| | % C14-CMC Removal by Cellulase |
|---|---|
| Detergent without cellulase (= reference) | 0 |
| Detergent + Celluzyme ® | |
| 1.5 mg protein/L (150 × $10^{-6}$%) | 12.7 |
| 3.0 mg protein/L (300 × $10^{-6}$%) | 17.7 |
| 4.5 mg protein/L (450 × $10^{-6}$%) | 21.5 |
| Detergent + 43 kD endoglucanase | 20.3 |
| 0.3 mg protein/L (30 × $10^{-6}$%) | |

Discussion of the Results

The above data clearly demonstrate the criticality of the claimed parameter for the cellulases of the invention over the commercially available Celluzyme.

EXAMPLE II

Two sets of each four types of detergent compositions are prepared, all based on a compact granular.

Such a compact granular detergent composition typically contains the following ingredients:

| | |
|---|---|
| Linear alkyl benzene sulphonate (LAS) | 11% |
| Alkyl suphate | 5% |
| Nonionic | 6% |
| Trisodium citrate | 15% |
| Zeolite | 32% |
| Citric acid | 6% |
| Polymer | 4% |
| Chelant | 0.2% |
| Sodium sulphate | 5% |

-continued

| | |
|---|---|
| Sodium silicate | 2% |
| Perborate | 0.5% |
| Phenol sulphonate | 0.1% |

The above detergent composition was supplemented as indicated in below:

SET 1 : With 43 kD endoglucanase

A) without 43 kD endoglucanase and peroxidase=reference
B) with 43 kD endoglucanase
C) with peroxide
D) with 43 kD endoglucanase and peroxidase SET 2 : With Celluzyme$^R$ A) without celluzyme® and peroxidase
B) with celluzyme®
C) with peroxidase
D) with celluzyme® and peroxidase The first type of each set of detergent compositions does not contain any cellulase and peroxidase (reference composition: A).

In the first set of detergent compositions the 43 kD endoglucanase is added at a level of 2 mg enzyme protein/liter of the wash solution (55 cevu/liter). In the second set of the detergent compositions the celluzyme® is added at a level of 76 mg enzyme protein/liter of the wash solution (55 cevu/liter).

Test Conditions
  Test in Miele washing machine
  Cotton program, low water level (18l), short cycle
  4 cycles
  Temperature 40° C.
  Composition of the Wash-load
    1) 1 kg clean load:
      150 g cotton (terry)
      150 g knitted cotton (underwear)
      200 g woven cotton
      300 g PE/cotton
      200 g PE
    2) For whiteness grading: 3 white, soiled, items (4 replicates each).
    3) 10 by 5 cm acid red 151 dye on nylon: To create a low dye transfer level.
    4) Prepared stains to provide a source of typical laundry soil.
  Hard water (15 grs/glln).
  Detergent concentration=0.6%.
Test Procedure The design of the test is such as to compare whiteness of the textile items, laundered cumulatively 4 times between the compositions to be tested and the reference composition. Three soiled items were used for this test. For each treatment of an item four replicates were used. The items to be examined are displayed on a flat, neutral colored grading surface parallel to the light source. As a light source a fluorescent light is used: 27 Philips "cold" color TL 40/57 producing 1080 WATTS of light designed to match with regular daylight (D65). The color T° is of 7400° K., the color reflectance is excellent (94) and the light output is 46 LM/W.

Differences are recorded in panel score units (psu), positive being performancewise better than the reference treatment.

Grading Scale (PSU Grading)

0=Equal
1=I think this one is better
2=I know this one is a little better
3=This one is a lot better
4=This one is a whole lot better The PSU grading data are statistical recount, an average of the 4 replicates is made, LSD (least significant difference) is mentioned in table I and II.

TABLE III

Test results: peroxidase/celluzyme ®

|  | B vs. A | C vs. A | D vs. A | LSD |
|---|---|---|---|---|
| 2 cycles AV | 0.28 | 1.67 s | 1.80 s | 0.61 |
| 3 cycles AV | 0.22 | 2.02 s | 2.26 s | 0.50 |
| 4 cycles AV | 0.68 | 2.48 s | 2.66 s | 0.76 |

TABLE IV

Test results: peroxidase/43 kD endoglucanase

|  | B vs. A | C vs. A | D vs. A | LSD |
|---|---|---|---|---|
| 2 cycles AV | −0.10 | 1.38 s | 1.97 s | 0.40 |
| 3 cycles AV | −0.30 | 2.25 s | 2.51 s | 0.46 |
| 4 cycles AV | 0.07 | 2.44 s | 2.97 s | 0.29 |

Conclusion

The above results clearly show that the peroxidase/43 kD combination of the present invention gives a statistically significant better performance than the sum of the individual actions of both ingredients.

EXAMPLE III to VIII

The following compositions are made.

a) Compact granular detergent: examples II to IV.

|  | EXAMPLES | |
|---|---|---|
|  | III | IV |
| Linear alkyl benzene sulphonate | 11.4 | 10.70 |
| Tallow alkyl sulphate | 1.80 | 2.40 |
| $C_{45}$ alkyl sulphate | 3.00 | 3.10 |
| $C_{45}$ alcohol 7 times ethoxylated | 4.00 | 4.00 |
| Tallow alcohol 11 times ethoxylated | 1.80 | 1.80 |
| Dispersant | 0.07 | 0.1 |
| Silicone fluid | 0.80 | 0.80 |
| Trisodium citrate | 14.00 | 15.00 |
| Citric acid | 3.00 | 2.50 |
| Zeolite | 32.50 | 32.10 |
| Maleic acid acrylic acid copolymer | 5.00 | 5.00 |
| DETMPA | 1.00 | 0.20 |
| Cellulase 43 kD endoglucanase | 0.03 | 0.025 |
| Alkalase | 0.60 | 0.60 |
| Lipase | 0.36 | 0.40 |
| Amylase | 0.30 | 0.30 |
| Sodium silicate | 2.00 | 2.50 |
| Sodium sulphate | 3.50 | 5.20 |
| PVP | 0.30 | 0.50 |
| Perborate | 0.5 | 1 |
| Phenol sulphonate | 0.1 | 0.2 |
| Peroxidase | 0.1 | 0.1 |
| Minors | up to 100 | | b) conventional granular detergent: examples V and VI

|  | EXAMPLES | |
|---|---|---|
|  | V | IV |
| Sodium linear $C_{12}$ alkyl benzene sulfonate | 6.5 | 8.0 |
| Sodium sulfate | 15.0 | 18.0 |
| Zeolite A | 26.0 | 22.0 |
| Sodium nitrilotriacetate | 5.0 | 5.0 |
| Cellulase 43 kD endoglucanase | 0.02 | 0.03 |
| PVP | 0.5 | 0.7 |
| TAED | 3.0 | 3.0 |
| Boric acid | 4.0 | — |
| Perborate | 0.5 | 1 |
| Phenol sulphonate | 0.1 | 0.2 |
| Peroxidase | 0.1 | 0.2 |
| Minors | up to 100 | | c) liquid detergent: examples VII and VIII

|  | EXAMPLES | |
|---|---|---|
|  | VII | VIII |
| $C_{12-14}$ alkenyl succinic acid | 3.0 | 8.0 |
| Citric acid monohydrate | 10.0 | 15.0 |
| Sodium $C_{12-15}$ alkyl sulphate | 8.0 | 8.0 |
| Sodium sulfate of C12–15 alcohol 2 times ethoxylated | — | 3.0 |
| $C_{12-15}$ alcohol 7 times ethoxylated | — | 8.0 |
| $C_{12-15}$ alcohol 5 times ethoxylated | 8.0 | — |
| Diethylene triamine penta (methylene phosphonic acid) | 0.2 | — |
| Oleic acid | 1.8 | — |
| Ethanol | 4.0 | 4.0 |
| Propanediol | 2.0 | 2.0 |
| Protease | 0.2 | 0.2 |
| Cellulase 43 kD endoglucanase | 0.2 | 0.05 |
| PVP | 1.0 | 2.0 |
| Suds suppressor | 0.15 | 0.15 |
| NaOH | up to pH 7.5 | |
| Perborate | 0.5 | 1 |
| Phenol sulphonate | 0.1 | 0.2 |
| Peroxidase | 0.4 | 0.1 |
| Waters and minors | up to 100 parts | |

What is claimed is:

1. A dye transfer inhibiting composition comprising an enzyme exhibiting peroxidase activity, a hydrogen peroxide or a hydrogen peroxide precursor compound, or an enzymatic system capable of generating hydrogen peroxide, an oxidizable substrate for said enzyme exhibiting peroxidase activity, and a cellulase, wherein said cellulase has the amino acid sequence shown in the appended sequence listing ID#2, which provides at least 10% removal of immobilized radioactive labeled carboxymethyl cellulose according to the C14CMC method at $25\times10^{-6}\%$ by weight of the cellulase protein in the test solution.

2. A dye transfer inhibiting composition according to claim 1 wherein the cellulase consists essentially of a homogeneous endoglucanase component which is immunoreactive with an antibody raised against a highly purified about 43 kD cellulase derived from *Humicola insolens*, DSM 1800, or which is homologous to said 43 kD endoglucanase.

3. A dye transfer inhibiting composition according to claim 2 wherein the endoglucanase component of said cellulase has an isoelectric point of about 5.1.

4. A dye transfer inhibiting composition according to claim 2 wherein the composition is combined with detergent ingredients to form a detergent composition and wherein said endoglucanase component is producible by a method comprising cultivating a host cell transformed with a recombinant DNA vector carrying a DNA sequence encoding said endoglucanase component or a precursor of said endoglucanase component, as well as DNA sequences encoding functions permitting the expression of the DNA sequence encoding the endoglucanase component, or a precursor thereof, in a culture medium under conditions permitting the expression of the endoglucanase component or precursor thereof and recovering the endoglucanase component from the culture.

5. A dye transfer inhibiting composition according to claim 3 wherein said cellulase is producible by a species of Humicola.

6. A detergent composition according to claim 4 wherein said host cell is a strain of a fungus selected from Tricloderuca or Aspergillus, or a yeast cell belonging to a strain of Hansenula or Saccharomyces.

7. A detergent composition according to claim 4 wherein said host cell is a strain of a bacterium, e.g. Bacillus, Streptomyces or $E.\ coli$.

8. A dye transfer inhibiting composition according to claim 1, wherein the hydrogen peroxide precursor is a perborate or percarbonate.

9. A dye transfer inhibiting composition according to claim 8 wherein the level of said perborate is from 1 μM–10 mM of the wash solution.

10. A dye transfer inhibiting composition according to claim 1, wherein said additional oxidizable substrate is selected from a metal ion, a halide ion or an organic compound such as a phenol, or a phenol sulfonate.

11. A dye transfer inhibiting composition according to claim 1, wherein said enzymatic system capable of generating hydrogen peroxide is an oxidase selected from the group consisting of glucose oxidase, urate oxidase, galactose oxidase, alcohol oxidases, amine oxidases, amino acid oxidase and cholesterol oxidase.

12. A dye transfer inhibiting composition according to claim 1, which is a detergent additive, in the form of a non-dusting granulate, a stabilized liquid, or a protected enzyme system.

13. A dye transfer inhibiting composition according to claim 12 which is in granular form, compact granular form or liquid form.

14. A process for inhibiting the transfer of a textile dye from a dyed fabric to another fabric when said fabrics are washed and/or rinsed together in a wash liquor, contacting said fabrics with a composition according to claim 1 above, the peroxidase being used at levels of from 0.01 to 100 mg/liter of wash solution, the level of hydrogen peroxide being from 0.001–5 mM of the wash solution, and the absolute level of additional oxidizable substrate being from 1 μM to 1 mM, and the cellulase being added at levels of from 0.005 to 40 mg enzyme protein/liter of wash solution.

* * * * *